US009018372B2

(12) United States Patent
Meier et al.

(10) Patent No.: US 9,018,372 B2
(45) Date of Patent: Apr. 28, 2015

(54) BONDING PRODUCTS OF AMINATED POLYSACCHARIDES

(75) Inventors: Bernd Horst Meier, Darmstadt (DE); Iris Jankowiak-Meier, Darmstadt (DE); Nele Meier, Darmstadt (DE); Clara Meier, Darmstadt (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 13/256,018

(22) PCT Filed: Mar. 31, 2010

(86) PCT No.: PCT/EP2010/054295
§ 371 (c)(1),
(2), (4) Date: Sep. 12, 2011

(87) PCT Pub. No.: WO2010/136242
PCT Pub. Date: Dec. 2, 2010

(65) Prior Publication Data
US 2012/0010391 A1    Jan. 12, 2012

(30) Foreign Application Priority Data

Mar. 31, 2009 (DE) .......................... 10 2009 015 085
Dec. 7, 2009 (WO) ................. PCT/EP2009/008718

(51) Int. Cl.
C07H 1/00 (2006.01)
C08B 37/08 (2006.01)
C08B 37/10 (2006.01)
A61K 31/726 (2006.01)
A61K 31/722 (2006.01)
A61K 31/736 (2006.01)
A61K 31/718 (2006.01)
A61K 31/715 (2006.01)
A61K 47/48 (2006.01)
A61K 49/00 (2006.01)

(52) U.S. Cl.
CPC ......... *A61K 47/4823* (2013.01); *A61K 49/0017* (2013.01)

(58) Field of Classification Search
USPC ......... 536/123.1, 55.1, 21, 20; 514/54, 56, 55
See application file for complete search history.

(56) References Cited

U.S. PATENT DOCUMENTS 7,541,328 B2    6/2009   Hemberger et al.
7,816,516 B2   10/2010   Sommermeyer et al.
2009/0053284 A1*  2/2009  Langer et al. ............... 424/426
2010/0298529 A1  11/2010  Meier et al.

FOREIGN PATENT DOCUMENTS

| EP | 0051354 A2 | 5/1982 |
|---|---|---|
| EP | 1 152 013 A1 | 11/2001 |
| EP | 1 994 945 A1 | 11/2008 |
| EP | 1 994 946 A1 | 11/2008 |
| WO | WO 9602260 A1 | 2/1996 |
| WO | WO 0172283 A1 | 10/2001 |
| WO | WO 02080979 A2 | 10/2002 |
| WO | WO 02080979 A3 | 10/2002 |
| WO | WO 03074087 A1 | 9/2003 |
| WO | WO 2004024761 A1 | 3/2004 |
| WO | WO 2007101698 A2 | 9/2007 |
| WO | WO 2007101698 A3 | 9/2007 |
| WO | WO 2007/122269 A1 * | 11/2007 |
| WO | WO 2007122269 A1 | 11/2007 |
| WO | WO 2009135888 A2 | 11/2009 |
| WO | WO 2009135888 A3 | 11/2009 |

OTHER PUBLICATIONS

Maier et al.; WO 2007/122269 A1; Nov. 1, 2007 (English Machine Translation).*
Article—Bajpai et al., "Dynamics of controlled release of heparin from swellable corsslinked starch microspheres," *J. Mater. Sci: Mater. Med.*, vol. 18, 2007, pp. 1613-1621.
Search Report for PCT/EP2010/054295 dated Oct. 5, 2010, 4 pages.
Article—Alexei V. Demchenko, "General Aspects of the Glycosidic Bond Formation," Handbook of Chemical Glycosylation: Advances in Stereoselectivity and Therapeutic Relevance, 2008 Wiley-VCH Verlag GmbH & Co. KGaA, 27 pages.
Abstract of European Patent—EP1230935 dated Aug. 10, 2005, 2 pages.
Article—Köse et al., "Low-Molecular-Weight Heparin-Conjugated Liposomes with Improved Stability and Hemocompatibility," *Drug Delivery*, vol. 5, 1998, pp. 257-264.
Abstract of Article—Yang Shumin, "Use of Oligosaccharides as a New Feed Additive in Animal Feeding: A Review," *ACTA Zoonutrimental Sinica*, vol. 11, No. 1, Jan. 1999 pp. 1-9.
Abstract of German Patent—DE10105921, Aug. 14, 2002, 1 page.
Abstract of Article—Lee et al., "Controlled dual release of basic fibroblast growth factor and indomethacin from heparin-conjugated polymeric micelle," *Int. J. Pharm.*, Jan. 4, 2008, vol. 346(1-2), pp. 57-63.

* cited by examiner

*Primary Examiner* — Shaojia Anna Jiang
*Assistant Examiner* — Michael C Henry
(74) *Attorney, Agent, or Firm* — Dority & Manning, P.A.

(57) ABSTRACT

The invention relates to a bonding product comprising at least the polysaccharides T1 and T2, characterized in that a) the monosaccharides from which the polysaccharides T1 and T2 are constructed are partially or completely bonded to each other alpha-1,4-glycosidically and b) at least one of the polysaccharides T1 and/or T2 comprises at least one amino group and c) T1 and T2 are chemically bonded to each other covalently by at least one linker Z and d) T1 and/or T2 carries m groups -(L-A), wherein A is an active pharmaceutical ingredient and/or a fluorescence label, L is a second linker, by which T1 and/or T2 is covalently bonded to A, and m is an integer, which is 0 or at least 1.

39 Claims, No Drawings

BONDING PRODUCTS OF AMINATED POLYSACCHARIDES

CROSS REFERENCE TO RELATED APPLICATION

This application is the national stage entry of International Patent Application No. PCT/EP2010/054295 having a filing date of Mar. 31, 2010, which claims priority to and the benefit of German Patent Application No. 10 2009 015 085.4 filed in the German Intellectual Property Office on Mar. 31, 2009 and International Patent Application No. PCT/EP2009/008718 having a filing date of Dec. 7, 2009, the entire contents of which are incorporated herein by reference.

The invention relates to a bonding product comprising at least the polysaccharides T1 and T2, wherein the monosaccharides from which the polysaccharides T1 and T2 are constituted are partially or completely linked together via alpha-1,4-glycosidic linkages, and at least one of polysaccharides T1 and/or T2 has an amino group, and T1 and T2 are bonded together chemically by covalent bonds through at least one linker Z.

In addition, the invention relates to pharmaceutical formulations comprising such a bonding product, wherein said pharmaceutical formulation can be applied for use in the prophylaxis of adhesions and scarring, and for stopping bleedings, or as a synovial fluid. In addition, the pharmaceutical formulations are intended for use in the therapy and prophylaxis of wound healing.

In addition, the invention relates to the use of the bonding product as a wound cover, implant and additive for hair gels, detergents and care agents, hair setting lotion, tinting agent and care agent, implant material, bone cement, as a matrix for epithelialization and colonialization by endogenous cells, suture material, vascular prostheses, vascular catheters, stents and central-venous catheters. Further, the invention relates to a process for preparing the bonding product.

In the medical field, plastic materials have come to be used in a wide variety of applications. For example, plastic materials are employed as implants, suture material, vascular prostheses, vascular catheters, or as an insulation material for electrical conductors. Frequently, the plastic materials employed are in constant contact with the tissues of the human body. However, a complex confrontation of the bodily defense systems of the implant bearer with the foreign body begins briefly after the implantation. The confrontation may lead to a rejection of the implanted foreign material, and to severe inflammation reactions in an unfavorable case. In addition, the implants can be infected by bacteria, which may lead to dissemination of the bacteria via the blood up to a life-threatening sepsis. Due to such complications, it is necessary that some implants are left in the body as shortly as possible. The problems lead to the use of plastic materials, which offer only small targets for immunological confrontation. Another difficulty resides in the activation of blood clotting by implants having contact with the circulating blood, such as vascular prostheses, stents or central-venous catheters. Clots formed by contact activation on implants can clog catheters and stents and thus render them unusable. Also, blood clots are very often the starting point of further bacterial colonialization. Attempts to overcome these complications include the coating of the blood-facing surface of the implants with anticoagulant substances, such as heparin. Some implants, such as stents, make it necessary to prevent this formation of blood clots by impeding the coagulation of blood by the additional intake of anticoagulant medicaments, such as phenprocoumon, clopidogrel, acetylsalicylic acid or heparins. This systemic anticoagulation is also associated with a substantial risk of bleeding. In a large number of central-arterial and central-venous catheters, shapeable plastic compounds, such as polyvinyl chloride or polyurethane compounds, are used. In these catheters having permanent contact with the circulating blood, the adhesion of coagulated bodies is counteracted by coating with anticoagulant substances and/or by a corresponding smoothing of the surface. In the coating of these plastic materials with heparins, various techniques from the charge-dependent deposition of the strongly negatively loaded heparin molecules to the chemically covalent bonding with formation of linkers may be used. Of all coatings with heparin, those methods are to be preferred that keep the anticoagulant portion of the heparin molecule free. However, the ideal coupling mode via the terminal aldehyde group of the heparin molecule can be realized only with increased expenditure due to the absence of suitable functional groups in the catheter material. Plastic materials are essentially biologically inert. Implants made of these plastic materials are rather recognized as foreign bodies and rejected than epithelialized by the body and converted in a way appropriate to the body, such as with implants of biological origin.

US 2005/828800 describes the reductive amination of hydroxyalkylcellulose compounds. The compounds described therein are solids consisting of anhydroglucose moieties linked together via beta-glycosidic linkages. Due to their physicochemical properties, these compounds are completely unsuitable for the purposes of the invention. A specific incorporation of further substituents through the introduced amino groups is not described. Rather, the reductively aminated hydroxyalkylcelluloses linked via beta-glycosidic linkages have a high similarity with the chitosans. As compared to chitosan, aminated celluloses are branched, and their glucosamine monomers are not acetylated at the amino groups like it is the case with chitosan in up to 40%, for example. However, both compounds are water-insoluble poly-beta-1,4-glucosamines. Higher mammals cannot degrade either beta-glycosidically linked chitosans or aminated hydroxyalkylcelluloses by endogenous enzymes. It is to be considered that the aminated hydroxyalkylcelluloses have a clearly higher allergic potential as compared to chitosan compounds. Other elastically shapeable polymers are employed in surgery as poly(methyl methacrylates), for example, as bone cement, with the above described risks of allergic reaction up to an allergic shock.

Therefore, there has been a need for providing suitable compounds that solve the problems mentioned in the prior art. In particular, it has been the object of the present invention to provide biologically degradable compounds that can be employed as polymeric base materials or additives, preferably in medicinal articles, and that can additionally be simply bonded with medicinally active substances and/or fluorescent markers.

Surprisingly, it has now been found that the problems of the prior art can be solved by a bonding product comprising at least two polysaccharides in which the monosaccharide moieties linked together via alpha-1,4-glycosidic linkages and which have at least one amino group.

Therefore, the present invention relates to a bonding product comprising at least the polysaccharides T1 and T2, wherein
a) the monosaccharides from which the polysaccharides T1 and T2 are constituted are partially or completely linked together via alpha-1,4-glycosidic linkages, and
b) at least one of polysaccharides T1 and/or T2 has at least one amino group, and c) T1 and T2 are bonded together chemically by covalent bonds through at least one linker Z; and
d) T1 and/or T2 bears m groups -(L-A), wherein
A is a medicinally active substance and/or a fluorescence marker;
L is a second linker through which T1 and/or T2 is covalently bonded with A, and
m is an integer of 0 or at least 1.

The bonding product according to the invention comprises at least two polysaccharides T1 and T2 constituted from monosaccharides partially or completely linked together via alpha-1,4-glycosidic linkages. In addition, at least one of the polysaccharides present in the bonding product bears at least one amino group.

The aminated polysaccharides represent ideal starting compounds for further bonding reactions with medicinally active substances, for example, or for bonding between the polysaccharides T1 and T2.

Preferably, the polysaccharides T1 and/or T2 are constituted from hexoses, especially aldohexoses, which may optionally be substituted. Thus, the monosaccharide moieties from which T1 and T2 are constituted may be partially or completely substituted and have one or more radicals, preferably selected from the group consisting of carboxylic acid, carboxylic acid ester, substituted or unsubstituted alkyl radicals with 1 to 4 carbon atoms, carboxylic acid amide, sulfonic acid, sulfonic acid amide and hydrogensulfate, and mixtures thereof. More preferably, the monosaccharide moieties at least in part have radicals selected from the group consisting of carboxymethyl, carboxyethyl, hydroxyethyl, hydroxymethyl, carboxylic acid, amide, sulfonamide, carboxylic acid salt, sulfonic acid salt, sulfuric acid, sulfate, hydrogensulfate and sulfuric acid amide, and mixtures thereof.

Preferably, suitable polysaccharides T1 and T2 that can be employed for building the bonding product according to the invention are independently selected from the group of optionally aminated polysaccharides consisting of amyloses, amylopectin, acemannan, arabinogalactans, galactomannans, alginic acid, alginic acid derivatives, alginic acid salts, galactoglucomannans, xanthans, carrageenan, guar gum, acacia gum, arabinogalactans, starch and modified starch. Under cost aspects, but also for reasons of biological tolerability, the polysaccharides T1 and T2 are independently selected, in particular, from optionally aminated polysaccharides from the group consisting of hydroxyalkyl starches, esterified starches, carboxyalkyl starches, hydroxyalkyl-carboxyalkyl starch, hydroxyethyl starch, carboxymethyl starch and hydroxyethyl-carboxymethyl starch.

In a preferred embodiment of the present invention, the bonding product according to the invention has the polysaccharides T1 and T2 that are independently selected from the group consisting of aminated hydroxyethyl starch, aminated carboxymethyl starch, aminated carboxyethyl starch, aminated hydroxyethyl-carboxymethyl starch, and aminated hydroxyalkyl starch.

In another preferred embodiment, the polysaccharides T1 and T2 of the bonding product according to the invention are different.

In another preferred embodiment, the optionally aminated polysaccharides T1 and/or T2 are water-soluble at 20° C., and preferably T1 and/or T2 have a water solubility at 20° C. of at least 1 g/l, preferably 10 g/l, especially 50 g/l.

The polysaccharides T1 and/or T2 have at least one amino group. In a preferred embodiment, both the polysaccharide T1 and the polysaccharide T2 has at least one amino group.

As amino groups, the polysaccharides T1 and/or T2 can have primary, secondary as well as tertiary amino groups. Preferably however, the polysaccharides T1 and/or T2 have at least one $-NH_2$ group.

The introduction of amino groups into polysaccharides is familiar to the skilled person. In a preferred embodiment, the amino groups are introduced by reductive amination of the polysaccharides T1 and/or T2. Thus, in a preferred embodiment, the polysaccharides T1 and/or T2 have amino groups that were introduced into the polysaccharides T1 and/or T2 by reductive amination. Such polysaccharides T1 and/or T2 can be recognized by the fact that the aldehyde groups of the polysaccharides T1 or T2 have been converted to amino groups, preferably $-NH_2$ groups, The polysaccharides T1 and T2, from which the bonding product is constituted, have monosaccharides that are partially or completely linked together via alpha-1,4-glycosidic linkages. The alpha-1,4-glycosidic linkage of the monosaccharides significantly contributes to a higher biological degradability of the polysaccharides. In a preferred embodiment, the monosaccharides from which the polysaccharides T1 and T2 are constituted are independently linked together via alpha-1,4-glycosidic linkages at at least 20%, preferably at least 50%, more preferably at least 90%, respectively based on the total number of monosaccharides.

The molecular weight of the polysaccharides T1 and T2 can vary depending on the application. Preferably, the average molecular weight of the polysaccharides T1 and/or T2 is within a range of from 20,000 to 800,000 dalton, preferably from 25,000 to 500,000 dalton, especially from 30,000 to 200,000 dalton.

Modified starch, especially hydroxyethyl starch, with a degree of substitution, DS, of from 0.2 to 0.8, preferably from 0.3 to 0.8, have been found to be particularly preferred polysaccharides T1 and/or T2, wherein the modified starch or the hydroxyethyl starch is optionally in an aminated form.

The degree of substitution, DS, is defined is defined as the ratio of the total number of substituted monomer units to the total number of monomer units.

As medicaments A, all substances may be used that can be incorporated in the above mentioned polysaccharides T1 and/or T2 through a linker L.

The bonding products according to the invention may optionally be linked with medicinally active substances or fluorescence markers. Preferably, the medicinally active substance is selected from the group consisting of antibiotics, antimicrobially active agents, cytostatic agents, chemotherapeutics, antigens, oligonucleotides, mediators, false metabolic substrates, and cytotoxic substances.

In a particularly preferred embodiment, the medicinally active substance A is selected from the group of glucosamineglycans or glucosamineglycan derivatives.

Especially for medicinal products, the use of medicinally active substances A has proven to be an advantageous feature of the bonding products.

In a particularly preferred embodiment, the medicinally active substance A is selected from the group consisting of heparin and heparin sulfate as well as hyaluronic acid, especially heparin or heparin sulfate with less than 6 saccharide moieties.

More preferably, the medicament A, especially heparin or heparin derivatives, is bonded by reductive amination with the polysaccharides T1 and/or T2, which may already be linked together through Z.

The polysaccharides T1 and/or T2 preferably have m groups -(L-A), wherein m is an integer of at least 1, preferably from 1 to 1000, especially from 1 to 100, more preferably from 2 to 100, and especially from 3 to 20.

The fluorescence markers are preferably selected from the group consisting of fluorescein isothiocyanate (FITC), phycoerythrin, rhodamide and 2-aminopyridine.

In addition to purely medicinally active substances, fluorescence markers, for example, fluorescein isothiocyanate, may also be therapeutically employed in connection with the polysaccharides T1 and/or T2. In the medical field, the marking with fluorescence markers can serve for specifically making these bonding products visible in the body. The use of the bonding products according to the invention in the cosmetic field may lead to, for example, hair gels, hair setting agents or tinting agents that shine under UV light. The polysaccharides T1 and T2 are bonded together chemically by covalent bonds through at least one linker Z. In a preferred embodiment of the present invention, the linker Z is a functional group selected from carboxylic acid ester, carboxylic acid amides, urethane, ether and amine, or includes at least one such functional group. More preferably, the covalent chemical linkage between T1 and T2 through the linker Z is reversible, i.e., can be cleaved again without difficulty, for example, enzymatically.

The second linker L, through which T1 and/or T2 is covalently linked with capital A also corresponds to the first linker Z in its function and design. For the linker L, it is particularly advantageous if it can be cleaved off again without difficulty, for example, enzymatically, which causes the medicinally active substance and/or the fluorescence marker to be released. The formation of the linker Z or L can be performed by means of methods described in the prior art for the formation of carboxylic acid esters, carboxylic acid amides, urethanes, ethers and amines.

If both T1 and T2 have amino groups, the bonding is preferably effected through aliphatic dialdehydes, for example, glutaraldehyde.

In a further embodiment of the present invention, the compound according to the invention is obtainable by a reaction of at least one free
  hydroxy group (—OH);
of the underlying polysaccharide T1 with a free
  isocyanate group (—NCO);
  carboxy group (—COOH);
  carboxylic acid halide group (—CO-A, with A=Cl, Br or I);
  alkylenecarboxy group (—(CH$_2$)$_q$—COOH, with q=1-10);
  ester group (—COOR with R=organic radical);
  epoxy group;
  or nucleophilic leaving group;
of the underlying polysaccharide T2 to form the linker Z, wherein said polysaccharide T1 and/or said polysaccharide T2 is linked with m groups -(L-A).

In another embodiment of the present invention, the compound according to the invention is obtainable by a reaction of at least one free
  amino group (—NH$_2$);
of the underlying polysaccharide T1 with a free
  isocyanate group (—NCO);
  carboxy group (—COOH);
  carboxylic acid halide group (—CO-A, with A=Cl, Br or I);
  alkylenecarboxy group (—(CH$_2$)$_q$—COOH, with q=1-10);
  ester group (—COOR with R=organic radical);
  epoxy group;
  or nucleophilic leaving group;
of the underlying polysaccharide T2 to form the linker Z, wherein said polysaccharide T1 and/or said polysaccharide T2 is linked with m groups -(L-A).

Further, in a preferred embodiment, the compound according to the invention is obtainable by a reaction of at least one free
  isocyanate group (—NCO);
  carboxy group (—COOH);
  carboxylic acid halide group (—CO-A, with A=Cl, Br or I);
  alkylenecarboxy group (—(CH$_2$)$_q$—COOH, with q=1-10);
  ester group (—COOR with R=organic radical);
  epoxy group;
  or nucleophilic leaving group;
of the underlying polysaccharide T1 with a free
  amino group (—NH$_2$)
of the underlying polysaccharide T2 to form the linker Z, wherein said polysaccharide T1 and/or said polysaccharide T2 is linked with m groups -(L-A).

More preferably, the compound according to the invention is obtainable by a reaction of at least one free
  hydroxy group (—OH); or
  amino group (—NH$_2$);
of the underlying polysaccharide T1 with a free
  isocyanate group (—NCO);
  carboxy group (—COOH);
  carboxylic acid halide group (—CO-A, with A=Cl, Br or I);
  alkylenecarboxy group (—(CH$_2$)$_q$—COOH, with q=1-10);
  ester group (—COOR with R=organic radical);
  epoxy group;
  or nucleophilic leaving group;
of the underlying polysaccharide T2 to form the linker Z, wherein said polysaccharide T1 and/or said polysaccharide T2 is linked with m groups -(L-A).

According to the present invention, nucleophilic leaving groups are preferably selected from the group of halides and tosylates.

Further, the compounds according to the invention can be obtainable by the reaction of a diamine of general formula I $$R^1(-NH_2)_2 \qquad (I)$$

wherein R' is selected from
a single bond;
linear or branched, saturated or unsaturated, aliphatic or alicyclic hydrocarbyl groups with 1 to 22 carbon atoms;
aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or heteroaryl, heteroaryl-C$_1$-C$_4$-alkyl and heteroaryl-C$_2$-C$_6$-alkenyl groups with 3 to 8 carbon atoms in the heteroaryl group and one or two heteroatom(s) selected from N, O and S, which may be substituted with C$_1$-C$_6$ alkyl and/or C$_2$-C$_6$ alkoxy groups;
with a free functional group of the underlying polysaccharide T1 and at least one free functional group of the underlying polysaccharide T2, which are independently selected from
  isocyanate group (—NCO);
  carboxy group (—COOH);
  carboxylic acid halide group (—CO-A, with A=Cl, Br or I);
  alkylenecarboxy group (—(CH$_2$)$_q$—COOH, with q=1-10);
  ester group (—COOR with R=organic radical);
  epoxy group;
  or nucleophilic leaving group;

to form the linker Z, wherein said polysaccharide T1 and/or polysaccharide T2 is linked with m groups -(L-A).

Suitable diamines include, for example, 1,2-diaminoethane, 1,2- or 1,3-diaminopropane, 1,2-, 1,3- or 1,4-diaminobutane, 1,5-diaminopentane, 2,2-dimethyl-1,3-diaminopropane, hexamethylenediamine, 1,7-diaminoheptane, 1,8-diamino-octane, trimethyl-1,6-diaminohexane, 1,9-diaminononane, 1,10-diaminodecane, 1,12-diaminododecane, 1,2-diaminocyclohexane, 1,4-diaminocyclohexane, 1,3-cyclohexanebis(methylamine), 1,2-phenylenediamine, 1,3-phenylenediamine, 1,4-phenylenediamine, 4,4'-ethylenedianiline, 4,4'-methylenedianiline, 4,4'-diaminostilbene, 4,4'-thiodianiline, 4-aminophenyldisulfide, 2,6-diaminopyridine, 2,3-diaminopyridine, 3,4-diaminopyridine, 2,4-diaminopyrimidine, 4,5-diaminopyrimidine, 4,6-diaminopyrimidine.

In addition, in a further embodiment of the present invention, the compounds according to the invention can be obtained by a reaction of a diol of general formula II

$$R^2(\text{—OH})_2 \quad (II),$$

wherein $R^2$ is selected from linear or branched, saturated or unsaturated, aliphatic or alicyclic hydrocarbyl groups with 2 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying polysaccharide T1 and at least one free functional group of the underlying polysaccharide T2, which are independently selected from
isocyanate group (—NCO);
carboxy group (—COOH);
carboxylic acid halide group (—CO-A, with A=Cl, Br or I);
alkylenecarboxy group (—$(CH_2)_q$—COOH, with q=1-10);
ester group (—COOR with R=organic radical);
epoxy group;
or nucleophilic leaving group;
to form the linker Z, wherein said colloid P and/or transport mediator T is linked with m groups -(L-A).

Suitable dials include, for example, ethylene glycol, propylene glycol, butylene glycol, and neopentylglycol, pentanediol-1,5, 3-methylpentanediol-1,5, bisphenol A, 1,2- or 1,4-cyclohexanediol, caprolactonediol (reaction product of caprolactone and ethylene glycol), hydroxyalkylated bisphenols, trimethylolpropane, trimethylolethane, pentaerythritol, hexanediol-1,6, heptanediol-1,7, octanediol-1,8, butanediol-1,4, 2-methyloctanediol-1,8, nonanediol-1,9, decanediol-1,10, cyclohexanedimethylol, di-, tri- and tetraethylene glycol, di-, tri- and tetrapropylene glycol, polyethylene and polypropylene glycols with an average molecular weight of from 150 to 15,000.

In another embodiment of the present invention, the compounds according to the invention are obtainable by a reaction of a dicarboxylic acid of general formula III

$$R^3(\text{—COOH})_2 \quad (III)$$

wherein $R^3$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying polysaccharide T1 and at least one free functional group of the underlying polysaccharide T2, which are independently selected from
amino group (—$NH_2$); or
hydroxy group (—OH)
to form the linker Z, wherein said polysaccharide T1 and/or polysaccharide T2 is linked with m groups -(L-A).

Suitable dicarboxylic acids include, for example, oxalic acid, malonic acid, succinic acid, glutaric acid, adipic acid, pimelic acid, azelaic acid, sebacic acid, maleic acid, fumaric acid, sorbic acid, phthalic acid, terephthalic acid, isophthalic acid, or agaric acid.

In particular, the compounds according to the invention may also be obtainable by the reaction of a dicarboxylic acid halide of general formula IV

$$R^4\text{—CO-A)}_2 \quad (IV)$$

wherein A=Cl, Br or I, and $R^4$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying polysaccharide T1 and at least one free functional group of the underlying polysaccharide T2, which are independently selected from
amino group (—$NH_2$); or
hydroxy group (—OH)
to form the linker Z, wherein said polysaccharide T1 and/or polysaccharide T2 is linked with m groups -(L-A).

In addition, in a further preferred embodiment, the compounds according to the invention are obtainable by the reaction of a diester of general formula V

$$R^5(\text{—COOR'})_2 \quad (V)$$

wherein R' is a $C_{1-10}$ alkyl group and $R^5$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with respectively one free functional group of the underlying polysaccharide T1 and at least one free functional group of the underlying polysaccharide T2, which are independently selected from amino group (—NH$_2$); or
hydroxy group (—OH)
to form the linker Z, wherein said polysaccharide T1 and/or polysaccharide T2 is linked with m groups -(L-A).

More preferably, the compounds according to the invention are obtainable by the reaction of a diisocyanate of general formula VI

$$R^6(-NCO)_2 \quad (VI)$$

wherein R$^6$ is selected from
linear or branched, saturated or unsaturated, aliphatic or alicyclic hydrocarbyl groups with 1 to 22 carbon atoms;
aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or heteroaryl, heteroaryl-C$_1$-C$_4$-alkyl and heteroaryl-C$_2$-C$_6$-alkenyl groups with 3 to 8 carbon atoms in the heteroaryl group and one or two heteroatom(s) selected from N, O and S, which may be substituted with C$_1$-C$_6$ alkyl and/or C$_2$-C$_6$ alkoxy groups;
with respectively one free functional group of the underlying polysaccharide T1 and at least one free functional group of the underlying polysaccharide T2, which are independently selected from
amino group (—NH$_2$); or
hydroxy group (—OH)
to form the linker Z, wherein said polysaccharide T1 and/or polysaccharide T2 is linked with m groups -(L-A).

Suitable diisocyanates include, for example, toluylene diisocyanate, bitoluylene diisocyanate, dianisidine diisocyanate, tetramethylene diisocyanate, hexamethylene diisocyanate, m-phenylene diisocyanate, m-xylylene diisocyanate, C$_1$-C$_6$ alkylbenzene diisocyanate, 1-chlorobenzene 2,4-diisocyanate, cyclohexylmethane diisocyanate, 3,3'-dimethoxydiphenylmethane 4,4'-diisocyanate, 1-nitrobenzene 2,4-diisocyanate, 1-alkoxybenzene 2,4-diisocyanate, ethylene diisocyanate, propylene diisocyanate, cyclohexylene 1,2-diisocyanate, 3,3'-dichloro-4,4'-biphenylene diisocyanate, diphenylene diisocyanate, 2-chlorotrimethylene diisocyanate, butylene 1,2-diisocyanate, ethylidene diisocyanate, diphenylmethane 4,4'-diisocyanate, diphenylethane diisocyanate, 1,5-naphthalene diisocyanate, cyclohexane diisocyanate and isophorone diisocyanate.

Particularly preferably, the compound according to the invention is obtainable by the reaction of a diepoxide with respectively one free functional group of the underlying polysaccharide T1 and at least one free functional group of the underlying polysaccharide T2, which are independently selected from
amino group (—NH$_2$); or
hydroxy group (—OH)
to form the linker Z, wherein said polysaccharide T1 and/or polysaccharide T2 is linked with m groups -(L-A).

In particular, 1,2,3,4-diepoxybutane or 1,2,7,8-diepoxyoctane have proven to be suitable diepoxides, preferably aliphatic diepoxides with 4 to 16 carbon atoms.

Bonding products in which the bonding of the T1 and T2 is effected by reductive amination have proven particularly advantageous. Thus, more preferably, the bonding products according to the invention are obtainable by reductive amination of a polysaccharide T1 having free amino groups (—NH$_2$) with a polysaccharide T2 having at least one aldehyde or keto group, and wherein the polysaccharide T1 and/or T2 is linked with m groups -(L-A).

Herein, the T1 having amino groups is preferably selected from the group consisting of aminated starch, aminated hydroxyalkyl starch, aminated hydroxyalkyl-carboxyalkyl starch, and aminated carboxyalkyl starch. Particularly preferred is aminated hydroxyalkyl starch, which may itself be obtained, for example, by reductive amination.

In a preferred embodiment, the bonding product according to the invention is obtainable by reductive amination of a polysaccharide T1 having free amino groups (—NH$_2$) with a polysaccharide T2 having at least one aldehyde or keto group, and wherein the polysaccharide T1 and/or T2 is linked with m groups -(L-A).

More preferably, the polysaccharide T1 having amino groups is selected from the group consisting of aminated starch, aminated hydroxyethyl starch, aminated hydroxyalkyl starch, aminated hydroxyalkyl-carboxyalkyl starch, and aminated carboxyalkyl starch. The medicinally active substance A is preferably heparin or a heparin derivative.

In a particularly preferred embodiment, the bonding product according to the invention is such that the medicinally active substance is heparin, m is at least 1, and the polysaccharide T1 and/or T2 is a hydroxyethyl starch, and the linker L is an —NH group.

In a preferred embodiment, the linker L is a functional group selected from carboxylic acid ester, carboxylic acid amide, urethane, ether and amine or comprises such a group.

Depending on the field of application, the polysaccharides T1 and T2 may also be linked through the linkers Z to form larger clusters. According to the invention, the ratio of this bonding reaction can be influenced by suitably modifying the process employed. For example, this can be done most simply by changing the ratio employed of the polysaccharides T1 and T2 as well as the bonding substrates employed, and by modifying the molecular weight of the polysaccharides T1 and T2 employed. In addition, reaction conditions such as the temperature, pressure and catalysts also influence the ratio of the two reactants. However, this is familiar to the skilled person. In a preferred embodiment, the bonding product comprises further polysaccharides in addition to the polysaccharides T1 and T2. However, in a particularly preferred embodiment, the bonding product comprises exclusively the polysaccharides T1 and T2, optionally linked with m groups -(L-A).

The bonding product of the present invention may be in the form of a liquid, hydrogel, film or solid. In a preferred embodiment, the bonding product is in the form of a polymeric solid and preferably has an average molecular weight of at least 50,000 daltons, preferably at least 100,000 daltons, especially from 120 to 2,000,000 daltons.

The bonding product of the present invention is obtainable by bonding together at least the polysaccharides T1 and T2, wherein the monosaccharides from which the polysaccharides T1 and T2 are constituted are partially or completely linked together via alpha-1,4-glycosidic linkages, and at least one of polysaccharides T1 and/or T2 has at least one amino group, at least one linker Z bonding together T1 and T2 chemically by covalent bonds, and wherein T1 and/or T2 bears m groups (L-A).

The present invention further relates to a pharmaceutical formulation comprising the bonding product according to the invention.

The pharmaceutical formulation may be used for the prophylaxis of adhesions and scarring. Surprisingly, it has been found that the application of the bonding product according to the invention in the form of a hydrogel can avoid scarring and especially adhesions. This is of great importance, in particular, in the postoperative care of patients.

In addition, the pharmaceutical formulations of the present invention can be used for stopping bleedings, or the pharmaceutical formulation is used as a synovial fluid.

In addition, it has surprisingly been shown that the bonding products of the present invention can be used in the therapy and prophylaxis of wound healing. Thus, it is preferred for the bonding products of the present invention to be used for wound covers. The product can be incorporated into the wound dressing as a hydrogel, solid or liquid. In addition, the bonding products according to the invention are used as implants. In particular, when the bonding products according to the invention were provided with heparin or heparin derivatives or hyaluronic acid, it has been found that they exhibit excellent properties, in particular, in medical articles in contact with the tissue or body fluids. The products according to the invention may also be added to implants or medical articles merely as an additive.

In addition, the present invention further relates to the use of the bonding product according to the invention as an additive for or for the preparation of hair gels, detergents and care agents, hair setting lotions, tinting agents and care agents, implant material, bone cement, as a matrix for epithelialization and colonialization by endogenous cells, suture material, vascular prostheses, vascular catheters, stents and central-venous catheters.

The present invention further relates to a process for preparing the bonding product according to the invention.

The process for preparing the bonding product according to the invention is effected by bonding at least one polysaccharide T1 with at least one polysaccharide T2 to form the linker Z through which T1 and T2 are covalently linked with one another, and wherein T1 and/or T2 bears m groups -(L-A), wherein A is a medicinally active substance and/or a fluorescence marker;
L is a second linker through which T1 and/or T2 is covalently bonded with A, and
m is an integer of 0 or at least 1.

To T1, T2, A, Z, L and m, the preferred embodiments as stated above apply.

In a preferred embodiment of the process according to the invention, the polysaccharides T1 and/or T2 are aminated hydroxyethyl starch and/or aminated carboxymethyl starch.

In a further preferred embodiment of the process according to the invention, the polysaccharides T1 and/or T2 are first linked to a medicinally active compound A, followed by effecting the formation of linker Z.

In a particularly preferred embodiment of the process according to the present invention, the process is carried out by the following steps:
a) reductive amination of a hydroxyethyl starch;
b) linking the aminated hydroxyethyl starch obtained in step a) with heparin by reductive amination; and
c) linking the product obtained in step b) with hydroxyethyl starch to form a linker Z.

More preferably, the linking of the polysaccharides T1 and/or T2 as defined above is effected through the second linker L with the medicinally active substance A. For producing the linker L to the medicinally active substance A, preferably heparin, preferably bifunctional and trifunctional molecules are employed that have identical or different functional groups capable of reacting with the functional groups of heparin, i.e., also with the functional groups of the polysaccharide(s). However, undesirable links between the heparin molecules and polysaccharide molecules themselves (cross-linking) may occur. These reaction products compete with the desirable links between heparin and polysaccharide T1 and/or T2. Therefore, bipolyfunctional molecules with different functional groups reacting with a functional group present only on heparin on the one hand or reacting with a functional group present only on the polysaccharide on the other hand are particularly suitable. This usually requires a corresponding chemical alteration on the part of the polysaccharide (T1 and/or T2), less frequently of the heparin. The yield of linking products according to the invention can be significantly increased by the immobilization of heparin to suitable attachment bodies.

For the carboxy groups present in carboxymethyl starches, compounds selected from the group of diepoxyalkanes, preferably having from 4 to 16 carbon atoms, especially 1,2,3,4-diepoxybutane, 1,2,7,8-diepoxyoctane, or alternatively glutaraldehyde, are employed as linkers. Under acidic pH values, preferably in the range of 2 to 4, diepoxyalkanes form ester linkages, while forming ether linkages in an alkaline pH range (pH>10). Glutaraldehyde reacts with ester linkages preferably at a pH below 4. For the formation of ester linkages, carboxyalkyl groups can be introduced into the starch polymers. Particularly preferred are carboxymethyl hydroxyethyl starches with a DS for carboxymethyl groups of from 0.03 to 0.1, and a DS for hydroxyethyl groups of from 0.2 to 0.3, and a molecular weight of from 30,000 to 300,000. In very small heparin molecules with 1 to 4 saccharide moieties, the bonding to the polysaccharide may cause the linear heparin molecule to extend freely from the polysaccharide.

In a particular embodiment of the present invention, amino groups are introduced into a hydroxyalkyl starch or carboxyalkyl starch by reductive amination. With the introduced amino groups of the polysaccharide, for example, the terminal aldehyde groups of the glucosaminoglucan, such as the heparin or the hyaluronic acid, can be introduced in such a way that the rest of the heparin molecule remains free. The amino groups introduced by reductive amination are also utilized for covalent binding with radicals having carboxy groups, terminal aldehyde groups, carboxylic acid halides, carboxyalkyls or esters.

The reductive amination of the alpha-1,4-glycosidically linked polysaccharides T1 and/or T2 is advantageously effected with ammonia, alkylamines, dialkylamines or ammonium hydroxide in the presence of a reduction catalyst. This reduction is preferably effected in a hydrogen atmosphere under elevated pressure and temperature conditions. For example, Raney nickel or cobalt/nickel catalysts and/or ruthenium catalysts are employed as catalysts. The pressures and temperatures employed in the reductive amination with hydrogen are within a range of from 80 to 250° C., preferably from 100 to 200° C., and pressures of from 2 to 50 bar, preferably from 5 to 20 bar. The aminated polyalkyl starch, for example, hydroxyalkyl starch, can be reacted, for example, with the aldehyde groups of medicaments, for example, heparin or heparin derivatives, to form an imine. In the next step, the imine is reduced to an amine. The amino group of the aminated polysaccharide then reacts with the aldehyde group of the medicinally active substance to form a Schiff base. The latter is reduced to an amine by a suitable reducing agent selected from the group of salt-containing hydrides, lithium aluminum hydride, lithium borohydride, sodium borohydride, or sodium cyanoborohydride. In this step, it must be considered that the aminated polysaccharides, for example, hydroxyalkyl starches, also have a terminal aldehyde group each. The use of aminated polysaccharides enables a further process in two steps. In a first separate step, the glucosaminoglucan designated for incorporation is oxidized to a lactone, which is linked with the amino group of the aminated hydroxyalkyl starch in a further step to form a carboxylic acid amide. Preferably, the process according to Hashimoto is used (Hashimoto et al., Kunststoffe, Kautschuk, Fasern, Vol. 9 (1992), pages 1271 to 1279), In a particularly preferred embodiment, the amino groups of the polysaccharides T1 and/or T2 can be used for covalent linking, especially of heparins.

The invention will be further illustrated by the following Examples, but without being limited thereto.

EXAMPLES

Example 1

200 g of a hydroxyethyl starch with a molecular weight of 50,000 and a molar substitution of 0.3 is charged into an autoclave together with a 27% ammonium hydroxide solution and together with 400 g of a nickel/copper/chromium catalyst having a nickel content of 75%, a copper content of 23% and a chromium content of 2%. The autoclave is pressurized with hydrogen over a period of 12 hours gradually with steps of 100 bar, 150 bar, 170 bar. Before each pressure increase, a sample is taken, dialyzed and freeze-dried.

The temperature is increased to 220° C. Subsequently, the mixture is removed, dialyzed and freeze-dried. 200 mg of heparin is dissolved in 5 ml of PBS (phosphate buffered saline), pH 7.5, and pipetted into a reaction vessel. 200 mg of the reductively aminated hydroxyethyl starch is dissolved in 10 ml of distilled water, and the solution is carefully added. Thereafter, 0.025 mg of sodium cyanoborohydride $NaBH_3CN$ is admixed. The Petri dish is carefully shaken. After 2 hours, again 0.025 mg of the sodium cyanoborohydride is added, and the mixture is carefully shaken until bubbles cease to rise. The addition of sodium cyanoborohydride is repeated four times in the same way. Thereafter, the reagent is allowed to stand for 72 hours; finally, it is taken up in an excess of PBS, pH=7.5, dialyzed and freeze-dried.

200 mg of the reagent is dissolved in 200 ml of distilled water. The mixture is adjusted to pH 10 by adding a 1 N NaOH/acetone solution (30/70), and shaken. 0.2 ml of 1,2,7,8-diepoxyoctane is pipetted into the vessel, followed by shaking. The addition of 0.2 ml of 1,2,7,8-diepoxyoctane is repeated every 10 hours. After 46 hours, the solution is removed, dialyzed against distilled water, and freeze-dried. The reagent is taken up in 10 ml of PBS; pH=7.5.

Example 2

200 g of a hydroxyethyl starch with a molecular weight of 50,000 and a molar substitution of 0.4 is dissolved in a 27% ammonium hydroxide solution.

The solution is charged into an autoclave together with 400 g of a nickel/copper/chromium catalyst. The autoclave is pressurized with hydrogen over a period of 12 hours gradually with steps of 100 bar, 150 bar, 170 bar. Before each pressure increase, a sample is taken, dialyzed and freeze-dried. The temperature is increased to 270° C. Subsequently, the mixture is removed, dialyzed and freeze-dried. The samples taken are dissolved in 5 ml of PBS (pH 7.5) together with 200 mg of heparin. 200 mg of the reductively aminated hydroxyethyl starch is dissolved in 10 ml of distilled water, and the solution is carefully added. Thereafter, 0.025 mg of sodium cyanoborohydride $NaBH_3CN$ is admixed. The Petri dish is carefully shaken. After 2 hours, again 0.025 mg of the sodium cyanoborohydride is added, and the mixture is carefully shaken until bubbles cease to rise. The addition of sodium cyanoborohydride is repeated four times in the same way. Thereafter, the reagent is allowed to stand for 24 hours. Finally, the reagent is taken up in an excess of PBS (pH=7.5), dialyzed and freeze-dried.

200 mg of a carboxymethyl starch with a DS of 0.4 is dissolved in 200 ml together with the reagent. The mixture is adjusted to pH 10 by adding a 1 N NaOH/acetone solution (30/70), and shaken. 0.4 ml of 1,2,7,8-diepoxyoctane is pipetted into the vessel, followed by shaking. After 12 hours, the solution is removed, dialyzed against distilled water, and freeze-dried. The reagent is taken up in 10 ml of PBS (pH=7.5).

Example 3

Linking of an aminated hydroxyethyl starch with fluorescence-marked heparin by reductive amination and linking of the reaction products together by another reductive amination with glutaraldehyde a) Coupling of heparin (HEP) with the fluorescence marker 2-aminopyridine To a solution of 2-aminopyridine (31.7 g, 0.33 mol, 1000 equ.) and $NaCNBH_3$ (2.1 g, 0.033 mol, 100 equ.) in formamide (50 ml), heparin (5.0 g) is added. The suspension obtained is stirred at 37° C. over night, and a clear solution is slowly formed. The reaction solution is poured onto EtOH (50 ml). The precipitated solid is filtered off and dried. Fluorescence-marked heparin (HEP*) is obtained as a slightly beige solid (1.3 g).

b) Amination of the hydroxyethyl starch (HES)
HES40→HES40-$NH_2$

HES40 (5.1 g, MW: 40 kDa) is dissolved in an aqueous ammonium hydroxide solution (100 ml, 22%). The catalyst consisting of nickel (5.6 g, 325 mesh), chromium (0.15 g, 100 mesh) and copper (1.8 g, 1 μm) is added to the solution. The mixture is stirred under a hydrogen atmosphere at 120° C. in an autoclave for 48 hours. After cooling to 20° C., the catalyst is filtered off, and the filtrate is poured onto ethanol (20 ml). The precipitated solid is filtered off, washed with little ethanol/water, and dried. The aminated HES is obtained as a slightly bluish solid (1.2 g).

c) Reductive amination of the HES obtained in step b) with the fluorescence-marked heparin (HEP*) obtained in step a)

HEP* (200 mg) is dissolved in an aqueous phosphate buffer solution (5 ml, pH=7.5), and a solution of the aminated hydroxyethyl starch from step b) (200 mg) in distilled water (10 ml) is added dropwise. At intervals of 2 hours, $NaCNBH_3$ is added six times (0.025 mg each, from an aqueous stock solution) to the reaction solution. The reaction mixture is again stirred at 20° C. for 2 hours. For further purification, the raw product is dialyzed for 24 hours. After removing the water by evaporation, the linking product of aminated HES and fluorescence-marked heparin is obtained as a colorless solid. Both in aqueous solution and as a solid, the compound shows an intensive green-yellow fluorescence when irradiated with UV light at 366 nm.

d) Reductive amination of several fluorescence-marked heparin/hydroxyethyl starch molecules obtained in steps a), b) and c) with glutaraldehyde The fluorescence-marked heparin/hydroxyethyl starch obtained in steps a), b) and c) (0.5 mg) is dissolved in an aqueous phosphate buffer solution (0.25 ml, pH=7.5) and mixed with glutaraldehyde (0.25 ml, 25% by weight) at 20° C. At intervals of 2 hours, $NaCNBH_3$ is added three times (0.01 mg each) to the reaction solution and dissolved by shaking. The mixture is allowed to stand over night. A beige precipitate is formed. The reaction product is precipitated with ethyl alcohol, and the solvent is evaporated. The solid shows a green-yellow fluorescence when irradiated with UV light at 366 nm.

Example 4

Linking of an aminated hydroxyethyl starch with fluorescence-marked heparin and hyaluronic acid by reductive amination and linking of the reaction products together by another reductive amination with glutaraldehyde Hyaluronic acid (2 mg) is dissolved in an aqueous phosphate buffer solution (1.5 ml, pH=7.5) and admixed with the reaction product from steps a), b) and c) of Example 3 dissolved in water. At intervals of 2 hours, NaCNBH$_3$ is added twice (0.01 mg each) to the reaction solution and dissolved by shaking. The mixture is allowed to stand over night.

Then, glutaraldehyde (0.25 ml, 25% by weight) is admixed at 20° C. At intervals of 2 hours, NaCNBH$_3$ is added twice (0.01 mg each) to the reaction solution and dissolved by shaking. The mixture is allowed to stand over night, dialyzed and freeze-dried.

Example 5

Linking of an Aminated HES with CMS

Two weight parts of the HES reductively aminated as in Example 3 is dissolved in an aqueous phosphate buffer solution (pH=7.5) together with 1 weight part of CMS (carboxymethyl starch), MW 100 kDa. At intervals of 2 hours, NaCNBH$_3$ is added four times (0.025 mg) to the reaction solution until a beige solid forms. The solvent is evaporated from the reaction product.

Reagents Employed in the Examples:

Heparin sodium salt (of porcine origin), pH=7, average MW=12-15 kDa, manufacturer: Changzhou Qianhong Bio-Pharma Co., Ltd., Jiangsu, China.

HES40: Hydroxyethyl starch having an average molecular weight MW=40 kDa, degree of substitution DS=0.3; manufacturer: BBraun, Crissier, Switzerland.

Sodium cyanoborohydride, NaBH$_3$CN, Acros Organics, New Jersey, USA.

Glutardialdehyde (25% by weight), Acros Organics, New Jersey, USA.

Heparin sodium salt (of porcine origin), pH=7, average MW=12-15 kDa, manufacturer: Changzhou Qianhong Bio-Pharma Co., Ltd., Jiangsu, China.

HES40: Hydroxyethyl starch having an average molecular weight MW=40 kDa, degree of substitution DS=0.3; manufacturer: BBraun, Crissier, Switzerland.

Sodium cyanoborohydride, NaBH$_3$CN, Acros Organics, New Jersey, USA.

Glutardialdehyde (25% by weight), Acros Organics, New Jersey, USA.

Hyaluronic acid from *Streptococcus equi*, Alfa Aesar, Ward Hill, Mass., USA.

The invention claimed is:

1. A bonding product comprising polysaccharides T1 and T2, characterized in that
   a) the monosaccharides from which the polysaccharides T1 and T2 are constituted are completely linked together via alpha-1,4-glycosidic linkages, and
   b) at least one of polysaccharides T1 and T2 has at least one amino group, and
   c) T1 and T2 are bonded together chemically by covalent bonds through at least one linker Z; and
   d) at least one of T1 and T2 bears m groups -(L-A), wherein
      A is a medicinally active substance selected from the group consisting of glucosaminoglycans and glucosaminoglycan derivatives;
      L is a second linker through which at least one of T1 and T2 is covalently bonded with A, and
      m is an integer of at least 1.

2. The bonding product according to claim 1, characterized in that the polysaccharides T1 and T2 are independently selected from the group of optionally aminated polysaccharides consisting of amyloses, amylopectin, acemannan, arabinogalactans, galactomannans, galactoglucomannans, xanthans, carrageenan, guar guru, acacia gum, arabinogalactans, starch and modified starch.

3. The bonding product according to claim 1, characterized in that the polysaccharides T1 and 12 are independently selected from optionally aminated polysaccharides from the group consisting of hydroxyalkyl starches, esterified starches, carboxyalkyl starches, hydroxyalkyl-carboxyalkyl starch, hydroxyethyl starch, carboxymethyl starch and hydroxyethyl carboxymethyl starch.

4. The bonding product according to claim 1, characterized in that the polysaccharides T1 and T2 are independently selected from the group consisting of aminated hydroxyethyl starch, aminated carboxymethyl starch, aminated carboxyethyl starch, aminated hydroxyethyl-carboxymethyl starch, and aminated hydroxyalkyl starch.

5. The bonding product according to claim 1, characterized in that the polysaccharides T1 and T2 have amino groups that were introduced by reductive amination.

6. The bonding product according to claim 1, characterized in that the polysaccharides T1 and T2 have at least one —NH$_2$ group.

7. The bonding product according to claim 1, characterized in that the monosaccharides from which the polysaccharides T1 and T2 are constituted are linked together via alpha-1,4-glycosidic linkages at least 20%, respectively based on the total number of monosaccharides.

8. The bonding product according to claim 1, characterized in that the polysaccharides T1 and/or T2 have an average molecular weight of from 20,000 to 800,000 dalton.

9. The bonding product according to claim 1, characterized in that the polysaccharides T1 and/or T2 have a modified starch, especially hydroxyethyl starch, with a degree of substitution, DS, of from 0.2 to 0.8.

10. The bonding product according to claim 1, characterized in that the medicinally active substance A is selected from the group consisting of antibiotics, antimicrobially active agents, cytostatic agents, chemotherapeutics, antigens, oligonucleotides, mediators, and cytotoxic substances.

11. The bonding product according to claim 1, characterized in that the medicinally active substance A is selected from the group consisting of heparin, heparin sulfate, and hyaluronic acid.

12. The bonding product according to claim 1, characterized in that the fluorescence marker is selected from the group consisting of fluorescein isothiocyanate (FITC), phycoerythrin, rhodamide and 2-aminopyridine.

13. The bonding product according to claim 1, obtainable by a reaction of at least one free
   isocyanate group (—NCO);
   carboxy group (—COOH);
   carboxylic acid halide group (—CO-A, with A=Cl, Br or I);
   alkylenecarboxy group (—(CH$_2$)$_q$—COOH, with q=1-10);
   ester group (—COOR with R=organic radical);
   epoxy group;
   or nucleophilic leaving group;
   of the underlying polysaccharide T1 with a free hydroxy group (—OH);
   of the underlying polysaccharide T2 to form the linker Z, wherein said polysaccharide T1 and/or said polysaccharide T2 is linked with m groups -(L-A).

14. The bonding product according to claim 1, obtainable by a reaction of at least one free
- hydroxy group (—OH);

of the underlying polysaccharide T1 with a free
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- of the underlying polysaccharide T2 to form the linker Z, wherein said polysaccharide T1 and/or said polysaccharide T2 is linked with m groups -(L-A).

15. The bonding product according to claim 1, obtainable by a reaction of at least one free
- amino group (—$NH_2$);

of the underlying polysaccharide T1 with a free
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- of the underlying polysaccharide T2 to form the linker Z, wherein said polysaccharide T1 and/or said polysaccharide T2 is linked with m groups -(L-A).

16. The bonding product according to claim 1, obtainable by a reaction of at least one free
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- of the underlying polysaccharide T1 with a free
- amino group (—$NH_2$);
- of the underlying polysaccharide T2 to form the linker Z, wherein said polysaccharide T1 and/or said polysaccharide T2 is linked with m groups -(L-A).

17. The bonding product according to claim 1, obtainable by a reaction of at least one free
- hydroxy group (—OH); or
- amino group (—$NH_2$);

of the underlying polysaccharide T1 with a free
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- of the underlying polysaccharide T2 to form the linker Z, wherein said polysaccharide T1 and/or said polysaccharide T2 is linked with m groups -(L-A).

18. The bonding product according to claim 1, obtainable by a reaction of a diamine of general formula I $$R^1(-NH_2)_2 \qquad (I)$$

wherein $R^1$ is selected from
- a single bond;
- linear or branched, saturated or unsaturated, aliphatic or alicyclic hydrocarbyl groups with 1 to 22 carbon atoms;
- aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or
- heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with a free functional group of the underlying polysaccharide T1 and at least one free functional group of the underlying polysaccharide T2, which are independently selected from
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- to form the linker Z, wherein said polysaccharide T1 and/or polysaccharide T2 is linked with m groups -(L-A).

19. The bonding product according to claim 1, obtainable by a reaction of a diol of general formula II $$R^2(-OH)_2 \qquad (II)$$

wherein $R^2$ is selected from
- linear or branched, saturated or unsaturated, aliphatic or alicyclic hydrocarbyl groups with 2 to 22 carbon atoms;
- aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or
- heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with a free functional group of the underlying polysaccharide T1 and at least one free functional group of the underlying polysaccharide T2, which are independently selected from
- isocyanate group (—NCO);
- carboxy group (—COOH);
- carboxylic acid halide group (—CO-A, with A=Cl, Br or I);
- alkylenecarboxy group (—$(CH_2)_q$—COOH, with q=1-10);
- ester group (—COOR with R=organic radical);
- epoxy group;
- or nucleophilic leaving group;
- to form the linker Z, wherein said colloid P and/or transport mediator T is linked with m groups -(L-A).

20. The bonding product according to claim 1, obtainable by a reaction of a dicarboxylic acid of general formula III $$R^3(-COOH)_2 \qquad (III)$$

wherein R³ is selected from a single bond;

linear or branched, saturated or unsaturated, aliphatic or alicyclic hydrocarbyl groups with 1 to 22 carbon atoms;

aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with a free functional group of the underlying polysaccharide T1 and at least one free functional group of the underlying polysaccharide T2, which are independently selected from amino group (—$NH_2$); or hydroxy group (—OH)

to form the linker Z, wherein said polysaccharide T1 and/or polysaccharide T2 is linked with m groups -(L-A).

21. The bonding product according to claim 1, obtainable by a reaction of a dicarboxylic acid halide of general formula IV

$$R^4(—CO-A)_2 \qquad (IV)$$

wherein A=Cl, Br or I, and R⁴ is selected from a single bond;

linear or branched, saturated or unsaturated, aliphatic or alicyclic hydrocarbyl groups with 1 to 22 carbon atoms;

aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_5$ alkoxy groups; or heteroaryl; heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with a free functional group of the underlying polysaccharide T1 and at least one free functional group of the underlying polysaccharide T2, which are independently selected from amino group (—$NH_2$); or hydroxy group (—OH)

to form the linker Z, wherein said polysaccharide T1 and/or polysaccharide T2 is linked with m groups -(L-A).

22. The bonding product according to claim 1, obtainable by a reaction of a diester of general formula V

$$R^5(—COOR')_2 \qquad (V)$$

wherein R' is a $C_{1-10}$ alkyl group and R⁵ is selected from a single bond;

linear or branched, saturated or unsaturated, aliphatic or alicyclic hydrocarbyl groups with 1 to 22 carbon atoms;

aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with respectively one free functional group of the underlying polysaccharide T1 and at least one free functional group of the underlying polysaccharide T2, which are independently selected from amino group (—$NH_2$); or hydroxy group (—OH)

to form the linker Z, wherein said polysaccharide T1 and/or polysaccharide T2 is linked with m groups -(L-A).

23. The bonding product according to claim 1, obtainable by a reaction of a diisocyanate of general formula VI

$$R^6(—NCO)_2 \qquad (VI)$$

wherein R⁶ is selected from linear or branched, saturated or unsaturated, aliphatic or alicyclic hydrocarbyl groups with 1 to 22 carbon atoms;

aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_5$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with respectively one free functional group of the underlying polysaccharide T1 and at least one free functional group of the underlying polysaccharide T2, which are independently selected from amino group (—$NH_2$); or hydroxy group (—OH)

to form the linker Z, wherein said polysaccharide T1 and/or polysaccharide T2 is linked with m groups -(L-A).

24. The bonding product according to claim 1, obtainable by a reaction of a diepoxide with respectively one free functional group of the underlying polysaccharide T1 and at least one free functional group of the underlying polysaccharide T2, which are independently selected from amino group (—$NH_2$); or hydroxy group (—OH)

to form the linker Z, wherein said polysaccharide T1 and/or polysaccharide T2 is linked with m groups -(L-A).

25. The bonding product according to claim 1, obtainable by reductive amination of a polysaccharide T1 having free amino groups (—$NH_2$) with a polysaccharide T2 having at least one aldehyde or keto group, and wherein the polysaccharide T1 and/or T2 is linked with m groups -(L-A).

26. The bonding product according to claim 25, characterized in that the polysaccharide T1 having amino groups is selected from the group consisting of aminated starch, aminated hydroxyalkyl starch, aminated hydroxyalkyl-carboxyalkyl starch, and aminated carboxyalkyl starch.

27. The bonding product according to claim 1, characterized in that the medicinally active substance is heparin or a heparin derivative.

28. The bonding product according to claim 1, characterized in that the medicinally active substance is heparin, the polysaccharide T1 and/or T2 is a hydroxyethyl starch, and the linker L is an —NH group.

29. The bonding product according to claim 1, characterized in that the linker L is a functional group selected from carboxylic acid ester, carboxylic acid amide, urethane, ether and amine or comprises such a group.

30. The bonding product according to claim 1, characterized in that the polysaccharides T1 and/or T2 are water-soluble at 20° C.

31. The bonding product according to claim 1, characterized by being in the form of a liquid, hydrogel, film or solid.

32. A pharmaceutical formulation comprising the compound according to claim 1.

33. The pharmaceutical formulation according to claim 32 for use in the prophylaxis of adhesions and scarring.

34. The pharmaceutical formulation according to claim 32 for use in the stopping of bleedings, or as a synovial fluid.

35. The pharmaceutical formulation according to claim 32 for use in the therapy and prophylaxis of wound healing.

36. A process for preparing a bonding product according to claim 1 by bonding at least one polysaccharide T1 with at least one polysaccharide T2 to form the linker Z through which T1 and T2 are covalently linked with one another, and wherein T1 and/or T2 bears m groups -(L-A), wherein
- A is a medicinally active substance selected from the group consisting of glucosaminoglycans and glucosaminoglycan derivatives;
- L is a second linker through which T1 and/or T2 is covalently bonded with A, and
- m is an integer of at least 1.

37. The process according to claim 36, characterized in that the polysaccharides T1 and/or T2 are aminated hydroxyethyl starch and/or aminated carboxymethyl starch.

38. The process according to claim 36, characterized in that the polysaccharides T1 and/or T2 are first linked to a medicinally active compound A, followed by effecting the formation of linker Z.

39. The process according to claim 36, comprising the following steps:
- a) reductive amination of a hydroxyethyl starch;
- b) linking the aminated hydroxyethyl starch obtained in step a) with heparin by reductive amination; and
- linking the product obtained in step b) with hydroxyethyl starch to form a linker Z.

* * * * *

UNITED STATES PATENT AND TRADEMARK OFFICE
CERTIFICATE OF CORRECTION

PATENT NO. : 9,018,372 B2
APPLICATION NO. : 13/256018
DATED : April 28, 2015
INVENTOR(S) : Bernd Horst Meier et al.

Page 1 of 1

It is certified that error appears in the above-identified patent and that said Letters Patent is hereby corrected as shown below:

In the Claims

Claim 2 (column 16, line 9)

"...thans, carrageenan, guar guru, acacia gum, arabinogalactans,..." should read --...thans, carrageenan, guar gum, acacia gum, arabinogalactans,...--

Signed and Sealed this
Eleventh Day of August, 2015

Michelle K. Lee
*Director of the United States Patent and Trademark Office*